United States Patent [19]

Janoski et al.

[11] 4,288,644

[45] Sep. 8, 1981

[54] PROCESS FOR ISOMERIZATION OF TETRAHYDRODIMETHYLDICYCLOPENTADIENE

[75] Inventors: Edward J. Janoski, Havertown; Abraham Schneider, Overbrook Hills; Richard E. Ware, Aston, all of Pa.

[73] Assignee: Suntech, Inc., Philadelphia, Pa.

[21] Appl. No.: 105,169

[22] Filed: Dec. 19, 1979

Related U.S. Application Data

[63] Continuation-in-part of Ser. No. 961,911, Nov. 20, 1978, abandoned, which is a continuation-in-part of Ser. No. 838,182, Sep. 30, 1977, abandoned.

[51] Int. Cl.³ .............................................. C07C 13/61
[52] U.S. Cl. .................................... 585/360; 585/22; 585/23
[58] Field of Search ............................ 585/22, 23, 360

[56] References Cited

U.S. PATENT DOCUMENTS

| | | | |
|---|---|---|---|
| 3,381,046 | 4/1968 | Cohen et al. | 585/360 |
| 4,059,644 | 11/1977 | Cannell | 585/360 |
| 4,177,217 | 12/1979 | Janoski et al. | 585/21 X |

*Primary Examiner*—Delbert E. Gantz
*Assistant Examiner*—Olik Chaudhuri
*Attorney, Agent, or Firm*—J. Edward Hess; Donald R. Johnson; Patrick C. Baker

[57] ABSTRACT

Tetrahydrodimethyldicyclopentadiene is catalytically isomerized to a liquid isomeric mixture having a suitable low temperature viscosity making it suitable as a missile fuel. The catalyst comprises an acidic alumina. Hydrogen is also present and in an amount sufficient to maintain the isomerization activity of the alumina. The elevated temperature is sufficient to cause isomerization.

10 Claims, No Drawings

PROCESS FOR ISOMERIZATION OF TETRAHYDRODIMETHYLDICYCLOPENTADIENE

BACKGROUND OF THE INVENTION

The invention herein described was made in the course of or under a contract thereunder with U.S. Air Force Systems Command.

CROSS-REFERENCE TO RELATED APPLICATION

This application is a continuation-in-part of U.S. Application Ser. No. 961,911, filed Nov. 20, 1978 now abandoned, which was a continuation-in-part of U.S. application Ser. No. 838,182, filed Sept. 30, 1977, now abandoned.

This invention relates to the isomerization of tetrahydrodimethyldicyclopentadiene, hereinafter referred to as THDMDCP. More particularly, the invention relates to preparation of an isomeric liquid mixture from THDMDCP. Still more particularly, the invention relates to the catalytic isomerization of THDMDCP to an isomeric liquid mixture. Generally the invention relates to the isomerization of endo-THDMDCP to exo-THDMDCP.

The aforementioned isomeric liquid mixture can be used as high energy missile fuel. Such fuels can be used in either jet or rocket propulsion. Jet propulsion includes a jet engine which can be used for a missile, an aircraft and others and includes the three basis types, i.e., ramjet, turbojet and pulse jet. The term rocket generally refers to a device containing its own oxygen or oxidizing agent. An article in Aviation Week and Space Technology, Jan. 26, 1976, pages 111-113, discloses some of the high density hydrocarbon fuels that are under consideration as missile fuels.

A precursor, dimethyldicyclopentadiene, hereinafter referred to as DMDCP, is prepared by dimerizing methylcyclopentadiene. The resulting dimethyl dimer mixture contains many isomers some of which can be represented by the following structures:

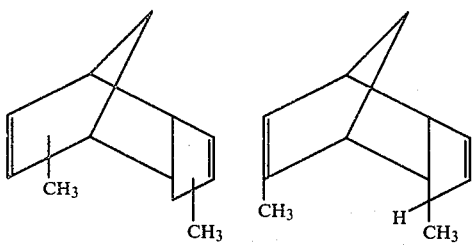

The foregoing structures are predominantly of endo stereo chemical configuration.

DMDCP can be hydrogenated to THDMDCP using hydrogen and a hydrogenation metal such as nickel, Raney Ni, palladium, and the like. The metals can be supported by such supports as carbon, silica-alumina and the like. They hydrogenation proceeds smoothly at a temperature of about 100°-400° C. and with a hydrogen pressure of about 200-5000 psig.

Some of the isomers are known to have substantially different melting points. For example the following two isomers are a clear liquid at ambient temperature,

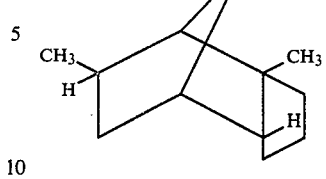

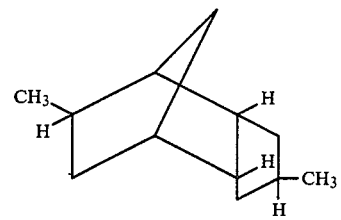

whereas the following two isomers are solid at room temperature and therefore have an adverse effect on the freezing point of the mixture.

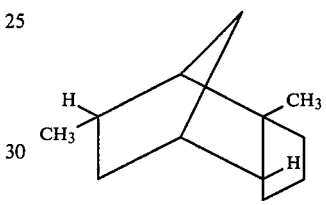

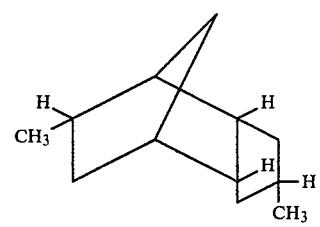

Thus, problem is how to isomerize the isomeric mixture from one which is not suitable as a missile fuel to an isomeric liquid mixture that is suitable.

U.S. Pat. No. 3,381,046 discloses the hydrogenation of DMDCP to THDMDCP using a variety of hydrogenation catalysts including palladium and nickel on Kieselguhr. It further discloses that the DMDCP can be partially hydrogenated and then thermally treated to convert the endo dihydro isomer to the exo dihydro isomer before finally hydrogenating the dihydro exo isomer to the tetrahydro exo isomer. Also the patent discloses that the endo dimer can be fully hydrogenated and then the tetra hydro endo isomer can be thermally treated in the presence of the hydrogenation catalyst to effect thermal isomerization to the tetrahydro exo isomer. The patent further discloses the use of acidic clay for isomerization but is silent as to the use of hydrogen with the clay.

However, applicants have discovered the following. If DMDCP is hydrogenated, at a suitable temperature, using a hydrogenation catalyst such as nickel on Kieselguhr, the olefinic materials deactivate the isomerization sites on the Kieselguhr. This deactivation is believed to be caused by the formation of polymers and/or carbon. Thus when the temperature of the mixture of hydrogenated DMDCP and the partially deactivated catalyst is raised to a conversion temperature the conversion from endo to exo is caused by a thermal effect rather than a catalytic one. Applicants have also discovered that to avoid this deactivation fresh catalyst should be used and that the catalytic isomerization is facilitated by the presence of hydrogen.

SUMMARY OF THE INVENTION

THDMDCP is catalytically isomerized using a catalytic amount of acidic alumina having isomeric activity. The isomerization occurs in the presence of sufficient hydrogen to maintain the catalytic activity of the acidic alumina and occurs at a suitable isomerization temperature. The isomerization causes the endo THDMDCP to form exo THDMDCP. As a result of the catalytic isomerization the resulting isomeric mixture has a high density and a suitable low temperature viscosity making it useful as a missile fuel.

DESCRIPTION

The process of this invention is for the catalytic isomerization of endo THDMDCP. It comprises contacting the endo material with a catalytic amount of acidic alumina having isomeric activity. The contacting occurs at a temperature at which isomerization occurs and in the presence of sufficient hydrogen to maintain the isomeric activity of the acidic alumina. The contacting is continued until the endo diene is isomerized to its exo isomer. The amount of isomerization can be inferred from the change in properties such as density and/or viscosity.

The isomerization of one of the THDMDCP's via the present invention can be represented by the following formula reaction:

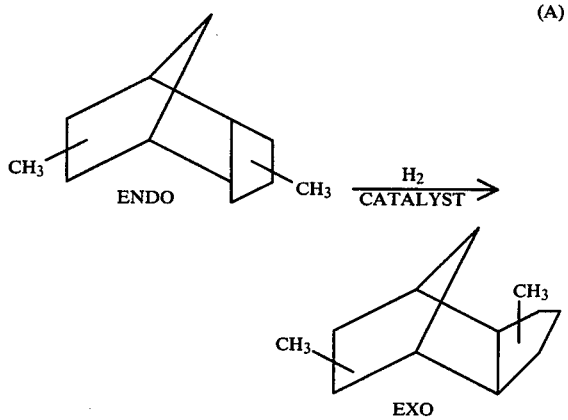

It can also be represented by the following formula reaction:

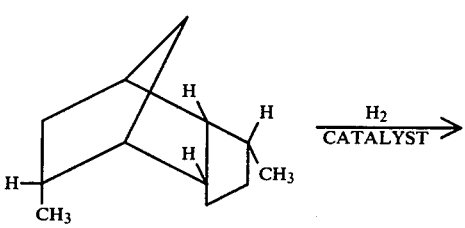

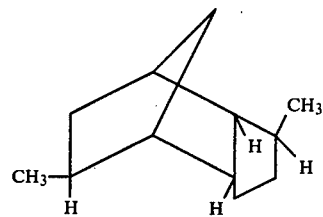

The exo compounds shown are but two of many possible isomers of THDMDCP that result via the isomerization.

While the THDMDCP feed can contain other similar hydrocarbons, such hydrocarbons should not adversely affect the isomerization or the catalyst. Further, the similar hydrocarbons should not adversely influence the desired resulting properties of the isomerized mixture. Thus, for optimum results, the feed consists essentially of THDMDCP which itself can be a mixture of THDMDCP isomers.

The catalyst used to isomerize the THDMDCP is an acidic alumina, including synthetic and natural forms. Preferred aluminas include silica-alumina, firebrick, Kieselguhr, and fire clay. The isomerization activity of the acidic alumina should not have been reduced by carbon and/or polymer formation on its active sites. Also present can be a hydrogenation metal such as palladium and nickel and these can be supported by such supports as carbon and silica-alumina. The amount of catalyst present is sufficient to catalytically direct, for example, reactions A and B. The preferred catalyst concentration can range between from about one-half part by weight of catalyst per hundred parts by weight of the THDMDCP to about a one to one ratio while a more preferred range is between from about 1:20 to about 1:10.

The amount of the nickel on silica-alumina can vary substantially; e.g., from about 0.5 wt.% to about 90 wt.%, while a preferred range is between from about 40 wt.% to about 90 wt.%. The silica-alumina weight ratio can also vary substantially; e.g., in the range between from about 1:30 to about 30:70. The amount of palladium on carbon or alumina can vary in the range between from about 0.25 wt.% to about 20 wt.%. When a catalyst mixture is used the weight ratio of acid clay or nickel on silica-alumina to the palladium on carbon can range between from about 1:50 to about 50:1. In the catalyst mixture the acid clay, firebrick, silica-alumina, or acidic alumina, supplies the acidic sites to cause the desired isomerization reaction to occur.

The isomerization temperature needs to be controlled between a narrow range. The lower limit can be determined by the rate of the reaction; i.e., if the temperature is too low the reaction rate is slow, and such a slow rate makes the process uneconomical. Thus, generally the lower temperature limit is about 100° C. with about 125° C. preferred. The upper limit is controlled by the formation of undesirable products which adversely affect the properties of the resulting missile fuel. Thus, generally the upper temperature limit is about 400° C. with about 350° C. preferred.

Hydrogen needs to be present. It keeps the isomerization sites of the catalyst clean and by doing so minimizes carbonization and polymerization. It should be present in a sufficient amount to perform its function. Generally a wide range of hydrogen pressure can be used, however, economic considerations favor using as low a pressure as possible.

The properties of the resulting isomerized liquid mixture can vary substantially depending upon the amount of isomerization that occurs. It can depend, in addition to the composition of the initial mixture, on how much of each of the particular isomer of THDMDCP is present. Typically, the resulting isomerizd THDMDCP mixture will have a density @ (20° C.)/4 in the range between from about 0.911 to about 0.918. The desired density of the missile fuel will depend, in part, on the particular missile design and such factors as the distance the missile is expected to travel.

As to viscosity, the isomeric mixture will typically have a kinematic viscosity @ 100° F. in the range between from about 2 cst to about 3 cst. The desired viscosity of a missile fuel will depend in part, on the particular missile design and whether the fuel will be heated during the flight and such factors as the altitude at which the missile will fly. The desired freezing point of the isomeric fuel mixture depends, in part, on the design of the missile operating conditions.

To obtain an isomerized mixture having a density and viscosity which make it useful as an additive for a high density fuel for an air-breathing missile, the reaction time or contacting time should be sufficient to obtain the desired properties. Sufficient time depends in part on the amount of the diene isomerized, the amount of stirring, the amount of catalyst used, the configuration of the vessel containing the reaction or contacting mixture, and other variables. The amount of isomerization can be monitored during the process by measuring, for example, the viscosity. Thus when the desired amount of isomerization has been obtained, the reaction can be stopped.

The following examples illustrate embodiments of the present invention. Also shown are comparative runs.

EXAMPLES

Accompanying Table I summarizes the operating conditions, runs 1–4, during the isomerization of THDMDCP. Also shown are the properties, i.e., density and viscosity of the resulting product. The products appear to have satisfactory freezing points. Also shown for comparative purposes is an unisomerized THDMDCP mixture having an unsatisfactory viscosity.

Runs 1, 3 and 4 indicated that the operating conditions used will result in an isomeric mixture of THDMDCP having densities and viscosities suitable for missile fuels. The resulting isomeric mixtures of runs 1–4 and the comparative run were analyzed by vapor phase chromatigraphy (vpc). These results are shown in accompanying Table II.

The accompanying Table II comparison of the vpc peaks indicates that peaks I and II represent the more desirable form of the THDMDCP isomers. While the isomeric product from run 3 does have more of the peak three material, it is believed that this could have resulted from less than optimal contacting time. By comparison the product of run 4, which was two hours longer than run 3, contains only a small amount of peak III. Also shown in Table II, for comparative purposes, is the aforementioned non-treated THDMDCP mixture. The vpc data shows that the non-treated mixture contains only small amounts of peaks I and II compared to the treated (isomerized) mixture of Runs 1–4.

The THDMDCP used in Run 1 was prepared in the following manner. 95.5 grams of DMDCP and 5 grams of fresh nickel (60%) on silica-alumina catalyst were placed in a 300 ml. autoclave (rocking type) reactor. The reactor was purged with nitrogen which in turn was purged with hydrogen. Then the reactor contents were pressured with hydrogen to 1480 psig at 23° C. and then heated to 275° C. with agitation. The reactor was maintained at 275° C. for ten hours. Makeup hydrogen was added during the ten hous to keep the reactor pressure at about 2000–2300 psig. Afterwards the reactor cooled and the hydrocarbon product was separated from the used catalyst. The hydrocarbon product was analyzed by vpc and found to be completely saturated and primarily THDMDCP.

The isomerization (Run 1) was performed using the following procedure. 68.4 grams of THDMDCP and 5 grams of fresh nickel (60%) on silica alumina catalyst were placed in a 300 ml. autoclave (rocking type) reactor. The reactor was purged with nitrogen and then with hydrogen. After purging the reactor was pressured to 1400 psig with hydrogen and then heated to 235° C. at which temperature the pressure was about 2350 psig. The reactor was maintained at 235° C. and 2350 psig for twenty hours. Afterwards the reactor and its contents were cooled and the reaction product was separated from the catalyst. The reaction product was a clear colorless liquid.

Run 3 was performed using the following procedure. 142 grams of DMDCP, 1.5 grams of palladium (10%) on carbon were placed in a 300 ml. autoclave (rocking type) reactor. The reactor was purged with nitrogen and then with hydrogen. Then reactor was pressured with hydrogen to 140 psig and then the temperature raised to 50°–60° C. and maintained at the aforementioned conditions for 5 hours. Vpc analysis indicated that complete hydrogenation had occurred, but that essentially no isomerization had occurred. The reactor and its contents were then cooled to room temperature and treated as follows.

At room temperature the cooled reactor was opened and 1.5 grams of fresh firebrick were added to the contents of the reactor. The reactor was purged and repressured with hydrogen and then heated to 235° C. at which temperature the pressure was 187 psig. After 17 hours at the aforementioned condition the pressure was lowered to 30 psig and the temperature increased to 240°–245° C. During the last 3 hours vpc analysis indicated that the isomerization rate was increasing. After a total of 6 hours at the higher temperature the reactor was cooled and the hydrocarbon contents separated from the catalyst.

Runs 2 and 4 were conducted in a manner similar to those described for run 3 and the results were as reported in the accompanying Tables.

Analogous isomerization results will be obtained when acidic alumina or silica-alumina, along with hydrogen, is used by itself.

The example which indicates the advantage of at least a minimum hydrogen pressure was as follows: A reactor was charged with 2800 mls. of THDMDCP and 63 grams of fresh nickel on silica-alumina as catalyst. Only a small amount of isomerization was observed after about 20 hours at 460° F. (238° C.) with a hydrogen pressure of about 200 psig. However, increasing the hydrogen pressure of the reactor to about 450 psig and using a slightly higher temperature of about 460°–470°

F., the isomerization was found to be complete after 14 additional hours.

TABLE I

ISOMERIZATION OF THDMDCP USING ACIDIC ALUMINA

| Catalyst[a] | Temp. °C. | H$_2$ Pressure psig | Time Hours | Density @ 20° C. 4 | Kinematic Viscosity @ 100° F. | Kinematic Viscosity @ −40° F. | Run |
|---|---|---|---|---|---|---|---|
| Ni-Si/Al | 235 | 2350 | 20 | 0.9136 | 2.72 | 37.3 | 1 |
| 10% Pd/C & Ni-Si/Al[b] | 240–245 | 105–145 | 18 | — | — | — | 2 |
| 10% Pd/C & Firebrick[b] | 235–240 | 30–187 | 20 | — | 2.63 | 30.8 | 3 |
| 10% Pd/C & Firebrick[b] | 245 | 49 | 22 | 0.9120 | 2.58 | 32.4 | 4 |
| Unisomerized THDMDCP Mixture | — | — | — | 0.9267 | 4.32 | — | — |

[a]The isomerization catalyst in all examples is a fresh catalyst.
[b]Ratio of Pd/C to other material is about one to one.

TABLE II

VPC ANALYSIS OF ISOMERIC PRODUCTS

| Peak Runs | Areas Under vpc Peaks Below I | I | II | III | IV |
|---|---|---|---|---|---|
| 1 | 1.3 | 33.3 | 47.1 | 13.6 | 4.7 |
| 2 | 5.2 | 41.7 | 52.3 | 0.8 | — |
| 3 | — | 44.6 | 22.4 | 27.3 | 5.7 |
| 4 | — | 51.1 | 44.7 | 4.1 | 0.1 |
| Unisomerized Mixture | — | 9 | 4 | 46 | 40 |

We claim:

1. Process for the catalytic isomerization of endo tetrahydrodimethyldicyclopentadiene comprising:
    (a) contacting endo tetrahydrodimethyldicyclopentadiene with a catalytic amount of acidic alumina having isomeric activity;
    (b) having the contacting occur at an isomerization temperature in the range of from about 100° C. to about 400° C. and in the presence of sufficient hydrogen to maintain the isomeric activity of the alumina; and
    (c) continuing the contacting until the endo diene is isomerized to its exo isomer.

2. Process according to claim 1 wherein in addition to the acidic alumina a hydrogenation metal is present.

3. Process according to claim 1 or 2 wherein the acidic alumina is silica-alumina.

4. Process according to claim 2 wherein the hydrogenation metal is palladium or nickel.

5. Process according to claim 2 wherein the catalyst is (1) a mixture of palladium on carbon and an acid clay; (2) a mixture of palladium on carbon and nickel on silica alumina; or (3) palladium on alumina, and the hydrogen has a pressure of at least about 30 psig.

6. Process according to claim 2 wherein the catalyst is a mixture of palladium on carbon and nickel on silica alumina and the hydrogen has a pressure of at least about 105 psig.

7. Process according to claim 2 wherein the catalyst is nickel on silica-alumina and the hydrogen has a pressure of at least about 200 psig.

8. Process according to claim 1 wherein the catalyst to the diene ratio ranges between from about one-half part by weight of catalyst per hundred parts by weight of the diene to about one to one.

9. Process according to claim 5, 6 or 7 wherein the resulting isomer mixture has a density (20° C.)/4 in the range between from about 0.911 to about 0.918.

10. Process according to claim 5, 6 or 8 wherein the resulting isomer mixture has a kinematic viscosity @ 100° F. in the range between from about 2 cst to about 3 cst.

* * * * *